(12) United States Patent
Brennan et al.

(10) Patent No.: US 6,183,249 B1
(45) Date of Patent: Feb. 6, 2001

(54) RELEASE SUBSTRATE FOR ADHESIVE PRECOATED ORTHODONTIC APPLIANCES

(75) Inventors: Joan V. Brennan, Sierra Madre; James D. Hansen, Pasadena, both of CA (US)

(73) Assignee: 3M Innovative Properties Company, St. Paul, MN (US)

( * ) Notice: Under 35 U.S.C. 154(b), the term of this patent shall be extended for 0 days.

(21) Appl. No.: 09/363,449

(22) Filed: Jul. 29, 1999

(51) Int. Cl.[7] .................................................. A61C 7/00
(52) U.S. Cl. .................................... 433/9; 206/369
(58) Field of Search ................... 433/9, 215; 206/368, 206/369, 460

(56) References Cited

U.S. PATENT DOCUMENTS

| | | |
|---|---|---|
| 4,204,325 * | 5/1980 | Kneble ...................................... 433/9 |
| 4,544,353 * | 10/1985 | Maurer et al. ............................ 433/9 |
| 4,675,232 | 6/1987 | Edenbaum et al. . |
| 4,733,659 | 3/1988 | Edenbaum et al. . |
| 4,927,361 | 5/1990 | Smith et al. . |
| 4,978,007 | 12/1990 | Jacobs et al. . |
| 5,015,180 | 5/1991 | Randklev . |
| 5,152,917 | 10/1992 | Pieper et al. . |
| 5,221,202 | 6/1993 | James . |
| 5,328,363 | 7/1994 | Chester et al. . |
| 5,348,154 | 9/1994 | Jacobs et al. . |
| 5,354,199 | 10/1994 | Jacobs et al. . |
| 5,429,229 | 7/1995 | Chester et al. . |
| 5,500,273 | 3/1996 | Holmes et al. . |
| 5,538,129 | 7/1996 | Chester et al. . |
| 5,552,177 | 9/1996 | Jacobs et al. . |
| 5,575,645 | 11/1996 | Jacobs et al. . |
| 5,636,736 | 6/1997 | Jacobs et al. . |
| 5,697,780 | 12/1997 | Tuneberg et al. . |
| 5,756,174 | 5/1998 | Tuneberg . |
| 5,827,058 | 10/1998 | Kelly et al. . |

FOREIGN PATENT DOCUMENTS

WO 95/15136    6/1995  (WO) .

* cited by examiner

*Primary Examiner*—Todd E. Manahan
(74) *Attorney, Agent, or Firm*—James D. Christoff

(57) ABSTRACT

A release substrate is releasably placed across a layer of adhesive that has been coated onto the base of an orthodontic appliance such as an orthodontic bracket. The release substrate enhances separation from the adhesive coated on the appliance such that the shape of the adhesive is essentially undisturbed and preferably substantially all of the adhesive remains on the base of the appliance when the substrate is detached from the adhesive. The release substrate is particularly suitable for use with adhesives that have a relatively low viscosity, adhesives that are more tacky and/or adhesives that have less cohesive strength than adhesives conventionally used with precoated orthodontic appliances.

65 Claims, 2 Drawing Sheets

RELEASE SUBSTRATE FOR ADHESIVE PRECOATED ORTHODONTIC APPLIANCES

BACKGROUND OF THE INVENTION

1. Field of the Invention

This invention broadly relates to orthodontic appliances that are precoated with an adhesive for facilitating bonding of the appliances to tooth structure. More particularly, the present invention concerns release substrates that are releasably connected to a layer of adhesive that has been coated onto a base of orthodontic appliances.

2. Description of the Related Art

Orthodontic treatment involves movement of malpositioned teeth to orthodontically correct positions. During treatment, tiny orthodontic appliances known as brackets are connected to surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth.

In the past, orthodontic appliances were connected to teeth by welding or brazing each bracket or buccal tube to a band that was then placed over the desired tooth in encircling relation. In more recent years, however, it has become common practice to bond orthodontic appliances directly to the surface of the tooth. Orthodontic brackets that are directly bonded to tooth surfaces provide a more aesthetic appearance than the appearance of brackets that are welded to bands, and help alleviate the problem of a "tinsel tooth" or "metallic mouth" appearance that is often associated with orthodontic treatment.

For many years, it was common practice to apply a layer of orthodontic adhesive to the base of directly-bonded appliances immediately before the appliances were placed on the tooth. In some instances, a quantity of adhesive was dispensed onto a mixing pad or dispensing well and a small spatula or other hand instrument was then used to apply a small dab of adhesive to each appliance. In other instances, a quantity of adhesive was dispensed from a syringe directly onto the base of the appliance.

Adhesive precoated brackets are also now available and represent a significant advantage to the orthodontist. Adhesive precoated brackets have a bonding base upon which the manufacturer has applied a precise quantity of adhesive such as a photocurable adhesive. When it is desired to mount the bracket on a tooth, the bracket is simply removed from the package and placed directly onto the tooth surface.

Examples of adhesive precoated brackets are described in U.S. Pat. Nos. 4,978,007, 5,015,180 and 5,328,363, all of which are assigned to the assignee of the present invention. In certain embodiments of the inventions described in those patents, the bracket and adhesive are packaged in a container that protects the adhesive from light, evaporation, oxidation, contamination, humidity and sublimation. In some of those embodiments, the coating of adhesive on the packaged bracket is in contact with a release liner or release coating that helps prevent the adhesive from being disturbed when the bracket is lifted from the package for use.

As can be appreciated, adhesive precoated brackets represent a significant time savings for the orthodontic practitioner because the adhesive need not be carefully applied to the base of each bracket before placement of the bracket onto the patient's tooth. In addition, the manufacturer can control the quantity of adhesive placed on the bracket so that there is sufficient adhesive to substantially fill the space between the bracket base and the tooth when the bracket is pushed into position, and yet there is not an inordinate amount of adhesive that might otherwise require excessive clean-up around the perimeter of the bracket base. Optionally, the adhesive is a light-curable adhesive so that the bracket can be carefully positioned in a proper orientation on the tooth surface before a curing lamp is activated to cure the adhesive and securely fix the bracket in place.

The packaged dental article described in the aforementioned U.S. Pat. No. 5,328,363 includes a dental appliance that is precoated with adhesive and located in a well of a container. In one embodiment of that patent, the adhesive rests on a flexible film made of a 0.05 mm thick sheet of fluorinated ethylene propylene copolymer ("Teflon" brand film), and the film is secured to the container at a location spaced from the appliance. As a consequence, the film tends to peel away from the adhesive when the appliance is removed from the container in order to inhibit separation of the adhesive from the appliance. Similar packaged articles using a polyester film instead of a fluorinated ethylene propylene copolymer film are also known.

In general, the adhesives used for adhesive precoated brackets that are received in a container or package having a release liner or coating are more viscous (i.e., less fluid) than other available orthodontic bonding adhesives, in part to ensure that the adhesive retains its shape and does not separate or distort when the bracket is lifted from the package for use. However, some orthodontists prefer the use of less viscous (i.e., more fluid) adhesives in order to facilitate manipulation of the bracket before the adhesive is cured. For example, brackets with less viscous adhesives are relatively easy to slide along the tooth surface when an effort is made to align the bracket in a proper, precise orientation on the tooth before the adhesive is cured.

Unfortunately, the flexible film described in the packaged article mentioned above, whether made of fluorinated ethylene propylene copolymer or polyester, is not always satisfactory for use with certain adhesives. For example, when soft, tacky, less viscous, hydrophilic adhesives are used, it has been found that a portion of the adhesive is sometimes left on the film when an attempt is made to lift the appliance from the container and detach the adhesive from the film. In those instances, there may not be a sufficient amount of adhesive remaining on the bracket to provide a bond strength adequate to retain the bracket on the tooth during the course of orthodontic treatment. Moreover, adhesives having a relatively low viscosity tend to slowly flow across the film and from the space beneath the bracket over extended periods of time, creating shelf life problems.

Additionally, when soft, tacky, less viscous adhesives are used with conventional adhesive precoated appliance packages, the shape of the adhesive may distort as the appliance is lifted from the container. In some instances, the adhesive once detached from the film may assume a configuration that is unsatisfactory for direct bonding unless additional steps are undertaken to shift the adhesive by hand back to its original, pillow-like shape. For example, when lifting the appliance from the container, some of the adhesive may be shifted to one side of the appliance base, such that the opposite side of the base does not have a satisfactory amount of adhesive for bonding. If the appliance is secured to the tooth in such a manner that a void space is present between a portion of the base and the opposed tooth surface, the void space may result in premature, spontaneous debonding of the appliance from the tooth, a nuisance that is best avoided. Furthermore, in some instances the void space can establish a pocket that receives food and debris, facilitating the formation of caries.

As can be appreciated, there is a need in the art to provide a release substrate for adhesive precoated appliances that would be satisfactory for use with a greater variety of adhesives than the release substrates that are presently known. Moreover, it would be an advantage to provide a release substrate for adhesive precoated orthodontic appliances that provides satisfactory results for use with adhesives that have a relatively low viscosity and/or are relatively tacky.

SUMMARY OF THE INVENTION

The present invention is directed toward a release substrate for adhesive precoated orthodontic appliances that is particularly suitable for use with adhesives that are less viscous, more tacky and/or have less cohesive strength than many of the adhesives currently used in connection with adhesive precoated orthodontic appliances. The release substrate of the invention enables the adhesive to be detached from the substrate whenever desired without undue distortion of the shape of the adhesive, and with little if any adhesive remaining on the substrate. In some instances, the adhesive may be detached from the substrate without the need for the peeling mechanics as described above.

In more detail, the present invention is directed in one aspect toward an article that comprises an orthodontic appliance having a base for bonding the appliance to a tooth. The article also includes an adhesive on the base of the appliance, and a release substrate having an exterior surface in contact with the adhesive. The exterior surface has a number of pores, and less than about 50% of the adhesive by weight is within the pores.

In another aspect, the invention also concerns an article that includes an orthodontic appliance having a base for bonding the appliance to a tooth. In this aspect, the article includes an adhesive on the base of the appliance, and a release substrate having an exterior surface in contact with the adhesive. The exterior surface includes a liquid composition. At least a portion of the liquid composition remains in contact with the adhesive when the appliance and the adhesive are released from the substrate.

An additional aspect of the present invention is directed toward an article that comprises an orthodontic adhesive having a base for bonding the appliance to a tooth and an adhesive on the base of the appliance. In this aspect, the article also includes a release substrate having an exterior surface in contact with the adhesive, and the release substrate comprises a foam.

The release substrate according to various embodiments of the invention can be satisfactorily used with a wide variety of adhesives in accordance with the preferences of the practitioner. Moreover, if desired, the release substrate can include components (such as curatives, antioxidants, filler particles, fluoride releasing materials etc.) that transfer to the adhesive as the adhesive is detached from the release substrate, and those components may advantageously enhance the properties or performance of the adhesive during the course of subsequent orthodontic treatment.

These and other aspects of the invention are described in more detail in the description that follows and are illustrated in the accompanying drawings.

DETAILED DESCRIPTION OF THE PREFERRED EMBODIMENTS

Figure 1:
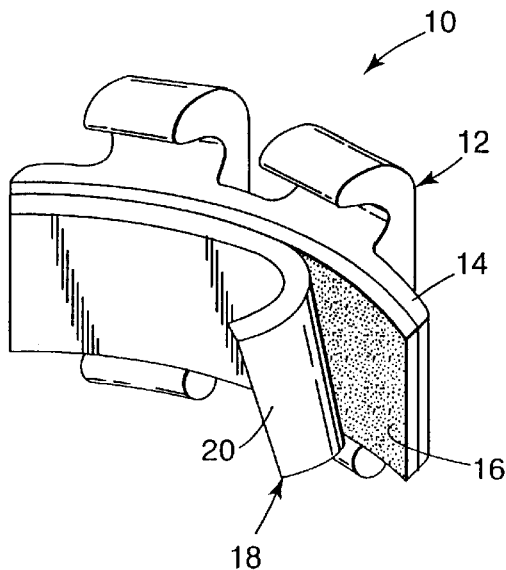
FIG. 1 is a perspective view of an orthodontic article according to one embodiment of the invention, wherein the article includes an orthodontic appliance, an adhesive on the base of the appliance and a release substrate in contact with the adhesive.

An orthodontic article according to one embodiment of the invention is illustrated in FIG. 1 and is broadly designated by the numeral 10. The article 10 includes an orthodontic appliance such as a bracket 12. The bracket 12 has a base 14 for direct-bonding the bracket 12 to a patient's tooth structure. Preferably, the base 14 has a slightly concave shape with a compound contour to precisely match the convex, compound contour of an external tooth surface.

The bracket 12 shown in FIG. 1 for exemplary purposes is a "twin tiewing" bracket having a pair of spaced apart gingival tiewings that are connected to one side of a bracket body and a pair of spaced apart occlusal tiewings that are connected to an opposite side of the bracket body. However, it should be understood in this regard that a "single tiewing" bracket having a single gingival tiewing and a single occlusal tiewing may also be used with the article 10 as an alternative to the bracket 12 illustrated in the drawings. The bracket 12 may be made of any one of a variety of materials, including metal (such as stainless steel), plastic (such as polycarbonate) or ceramic (such as monocrystalline or polycrystalline alumina). If made of plastic or ceramic, the bracket 12 is preferably transparent or translucent such that the color of the patient's tooth is visible through the bracket 12.

As additional alternatives, other types of appliances may be used with the article 10 in substitution for the bracket 12. For example, the appliance may be an orthodontic buccal tube that is adapted to be secured to one of the patient's molar teeth. As other alternatives, the appliance may be a button, a lingual sheath or any other device adapted to be bonded directly to the patient's tooth structure.

An orthodontic adhesive 16 extends across the base 14 of the bracket 12. The adhesive 16 has sufficient strength when hardened to secure and retain the bracket 12 on a patient's tooth structure during the typical course of an orthodontic treatment program. Preferably, the shape of the adhesive 16 resembles a pillow with four edge sections that are in approximate alignment with the four edge sections of the base 14. The adhesive 16 is also present in sufficient quantity to ensure that all of the space between the base 14 and the patient's tooth structure is filled with adhesive 16 once the base 14 has been forcibly placed onto the tooth structure and the adhesive 16 has hardened.

The adhesive 16 may be any one of a number of commercially available orthodontic adhesives useful for direct bonding, including adhesives having a relatively low viscosity. Suitable adhesives include, for example, Transbond XT brand adhesive from 3M Unitek, or Light Bond brand adhesive from Reliance.

The article 10 also includes a release substrate 18 that extends across the adhesive 16. The release substrate 18 includes an exterior surface 20 in contact with the adhesive 16. Preferably, the exterior surface 20 has cells, particles, protruding pins, projections or other structure that provides a number of pores at least in areas in contact with the adhesive 16. The pores may be separated and spaced from each other in non-communicating relation. Alternatively, the pores may be in communication with each other, either in a reference plane extending along the outermost portion of the exterior surface, or in one or more reference planes extending below such outermost portion, or in any combination of such planes.

Preferably, a majority of the volume of the pores does not contain adhesive. More preferably, the pores are substantially free of the adhesive 16. Preferably, less than about 50% of the adhesive by weight is within the pores, and more preferably less than about 75% of the adhesive by weight is within the pores. Most preferably, less than about 90% of the adhesive by weight is within the pores. Preferably, at least 50% of the volume of the pores is free of adhesive, and more preferably at least 75% of the volume of the pores is free of adhesive. Most preferably, at least 90% of the volume of the pores is free of adhesive. Such construction facilitates release of the adhesive 16 from the exterior surface 20.

The release substrate 18 may be made of any one of a number of materials. Particularly preferred materials include polymeric foams having either an open cellular structure or a closed cellular structure. A closed cell foam is preferred. The release substrate 18 is preferably compressible and preferably resilient.

Preferably, the exterior surface 20 of the release substrate 18 has pores having a diameter that are mostly, if not entirely, within the range of about 0.00005 inch (0.006 mm) to about 0.03 inch (0.76 mm). More preferably, the diameter of the pores is mostly, if not entirely, within the range of about 0.001 inch (0.02 mm) to about 0.01 inch (0.2 mm). An example of a suitable average pore size is 0.004 inch (0.1 mm) in diameter or alternatively in the range of about 0.006 inch (0.15 mm) to about 0.01 inch (0.2 mm). The pore size is determined by determining its diameter in a reference plane parallel to the plane of the exterior surface 20. If the pore does not present a circular shape in that reference plane, the pore size is determined by calculating the diameter of a circle presenting an area that is equal to the area of the pore in such reference plane.

Particularly preferred foam materials for the release substrate 18 include polyolefin foams such as polyethylene foams, polybutylene foams and polypropylene foams, or blends of the foregoing. Polyvinyl chloride foams, polyurethane foams and foam copolymers may also be employed. Examples of suitable polyethylene foams include L series, M series, S series and T series Minicel brand foams (such as series M200, M300 and T300) from Voltek. Optionally, an outer layer of cells of the foam may be heated to "seal" or shrink the size of the pores by reducing the pore diameter and/or by reducing the pore depth in directions perpendicular to the plane of the exterior surface 20.

If the selected foam is shown to absorb one or more of the fluid components of the adhesive 16 over time, then the foam could be modified in some manner provided the release characteristics of the foam are not unduly impaired. For example, the exterior surface 20 could be fused or coated with an organic or inorganic barrier material to partially close some or all of the pores. Optionally, the barrier material is a curable monomeric system that is cured or partially cured to establish a crosslinked barrier, either at the exterior surface 20, in the body of the foam material, or both. As another option, the foam is coated or partially coated (and possibly immersed) in a liquid component that reduces the driving force for absorption.

It has been observed that the use of foam for the release substrate 18 (and particularly the use of the Minicel brand foams mentioned above) impedes lateral flow of the adhesive 16, even in instances when the adhesive 16 has a relatively low viscosity. Such resistance to flow is a distinct advantage since the adhesive 16 better retains its original shape and the "footprint" of the adhesive is not unduly enlarged. The resilient, elastic nature of the foam also enhances peeling of the substrate 18 away from the adhesive 16 when desired, although a peeling motion is not essential for release.

The release substrate 18 may alternatively be made of other materials as well. For example, the release substrate 18 may be made of other polymers, copolymers or blends of polymers and copolymers such as polyesters, polyolefins, polyurethanes, fluoropolymers, (meth)acrylic, silicones, epoxies, synthetic rubbers, polycarbonates or vinyls. The release substrate 18 may also be made of ceramic, glass or metal.

When the release substrate 18 is made of a material other than a foam as described above, the pores in the preferred embodiments mentioned above may be made using any other suitable process or structure. For example, a number of particles such as spherical or irregularly-shaped beads, shards or particles made of glass, ceramic, metal or other materials may be fixed to a backing layer of the release substrate 18 to provide pores. As another alternative, the exterior surface 20 may have ridges, projections or other structure, either random or repeating, to provide a number of small pores. The pores may be made using a microreplication technique, such as the methods disclosed in U.S. Pat. Nos. 5,152,917 and 5,500,273.

Optionally, the release substrate 18 is constructed so that the pores extend only an area beneath the base 14 of the bracket 12. If desired, the release substrate 18 may include flanges, rims or other projections or recessed structure having a configuration adapted to surround the periphery of the base 14 when the bracket 12 is received on the substrate 18. For example, if the bracket base 14 presents a rectangular configuration in bottom view, the substrate 18 may include four elongated flanges that extend along the four sides of the base 14. Such structure may provide an advantage in hindering lateral movement or flow of the adhesive 16 and/or hindering movement of the bracket 12 relative to the substrate 18.

As another option, the release substrate 18 includes a quantity of a liquid composition that extends across the exterior surface 20 and is in contact with the adhesive 16. The liquid composition may be either a contiguous layer of liquid or a non-contiguous layer, such a patterned or printed coating or a coating randomly applied. The liquid composition may be made of any liquid material that facilitates release of the adhesive 16 from the substrate 18 when desired, and if curable may be uncured, partially cured or entirely cured when present in the article 10.

Preferably, the liquid composition is at least partially removed from the release substrate when the adhesive 16 detaches from the substrate 18, and remains with the adhesive 16 during bonding of the bracket 12 to the patient's tooth. Preferably, the liquid composition enhances the properties of the adhesive 16. For example, the liquid composition transferred to the adhesive 16 may increase the tackiness of the adhesive 16, may increase the wettability of the adhesive 16 and/or may increase the moisture tolerant characteristics of the adhesive 16. These enhanced properties may facilitate bonding of the bracket 12 and also decrease the likelihood of spontaneous debonding of the bracket 12 during the course of orthodontic treatment.

Particularly preferred liquid compositions include hydrophilic compositions that are compatible with the adhesive 16, such as some of the liquid orthodontic primers that are commercially available. An example of a suitable primer is Transbond MIP brand primer from 3M Unitek. Such primers not only enhance release of the adhesive 16 from the substrate 18 but also facilitate bonding of the bracket 12 to the patient's tooth.

The liquid composition may include one or more monomers, oligomers, polymers or copolymers or mixtures of the foregoing. The liquid composition may also contain additives such as pigments, antioxidants and/or curatives (to enhance curing properties of the adhesive 16). The liquid composition optionally contains solid filler particles such as fumed or fused silica, fluoroaluminosilicate, quartz, zirconia, and the filler particles could optionally be coated for example with silane, zirconate or titanate coatings as dispersion aids. The liquid composition may also include a fluoride releasing material such as zinc fluoride. As another option, the liquid composition may include a material that serves to etch the tooth enamel when placed into contact with a tooth.

Preferably, the liquid composition includes hydrophilic monomers, oligomers, polymers or blends thereof that optionally have the ability to absorb moisture and also provide enhanced chemical bonding to tooth enamel. Preferably, the liquid composition "cures into" the adhesive 16 as the adhesive hardens, i.e., the liquid composition polymerizes with the adhesive. Optionally, the liquid composition is wholly or partially crosslinked into the adhesive as the adhesive hardens. Furthermore, the liquid composition is preferable immiscible with the adhesive over an extended period of time, so that the liquid composition does not unduly mix with or dissolve into the adhesive before the adhesive cures.

Preferred moisture tolerant or hydrophilic materials for the liquid composition include 2-hydroxyethyl acrylate, 2-hydroxyethyl methacrylate ("HEMA"), hydroxypropyl acrylate, hydroxypropyl methacrylate, glycerol di-acrylate, glycerol di-methacrylate, polyethylene glycol mono methacrylate, polypropylene glycol mono methacrylate, tetrahydrofurfuryl acrylate, tetrahydrofurfuryl methacrylate, glycidyl acrylate, glycidyl methacrylate and the like. Other preferred hydrophilic monomers include glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate [where the number of repeating ethylene oxide units vary from 2 to 30, especially triethylene glycol dimethacrylate ("TEGDMA").

More specific examples of hydrophilic materials are nonionic polymers or copolymers, e.g. polyalkylene oxides (polyoxymethylene, polyethyleneoxide, polypropylene oxide) polyethers (polyvinylmethyl ether), polyethyleneimine copolymers, polyacrylamides and polymethacrylamides, polyvinylalcohol, saponified polyvinylacetate, polyvinylpyrrolidone, polyvinyloxazolidone, polymers containing N-oxysuccinimdo groups, ionic or ionizable polymers and copolymers containing polyacrylic acid, polymethacrylic acid in unionized, partially neutralized or fully neutralized form, polyethyleneimine and its salts, polyethylene sulfonic acid and polyaryl sulfonic acids in unionized, partially neutralized or fully neutralized form, polyphosphoric and polyphosphonic acids in unionized, partially neutralized or fully neutralized form.

Preferred hydrophilic materials may be prepared by reaction of vinylic monomers such as acrylates, methacrylates, crotonates, itaconates and the like that contain polar groups that are acidic, basic or provided as a salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quaternary ammonium, carboxylate salt, sulfonic acid salt and the like) and the precursors and protected forms of these groups.

Additional information regarding suitable hydrophilic materials may be found in applicant's pending U.S. application Ser. No. 09/311,606, which is incorporated by reference herein.

The liquid composition on the release substrate 18 provides a number of significant advantages. As mentioned above, the liquid composition may improve handling and/or bonding characteristics of the adhesive 16. The liquid composition may also eliminate the need in certain instances for a separate step of pre-applying a primer or wetting agent to the tooth surface before the adhesive 16 is placed in contact with the tooth. More specifically, pre-application of a primer or wetting agent to the tooth surface in traditional manner can be avoided if a sufficient amount of the liquid composition is transferred from the release substrate 18 to the tooth surface and the liquid composition has primer or wetting agent characteristics. Additionally, if the liquid composition sufficiently facilitates release of the adhesive 16, the provision of pores or cells on the release substrate 18 may be avoided.

An orthodontic article 10a constructed in accordance with another embodiment of the invention includes an appliance such as a bracket 12a having a base 14a. The article also includes an adhesive 16a on the base of the bracket 12a. A release substrate 18a has an exterior surface that is in contact with the adhesive 16a.

Figure 2:
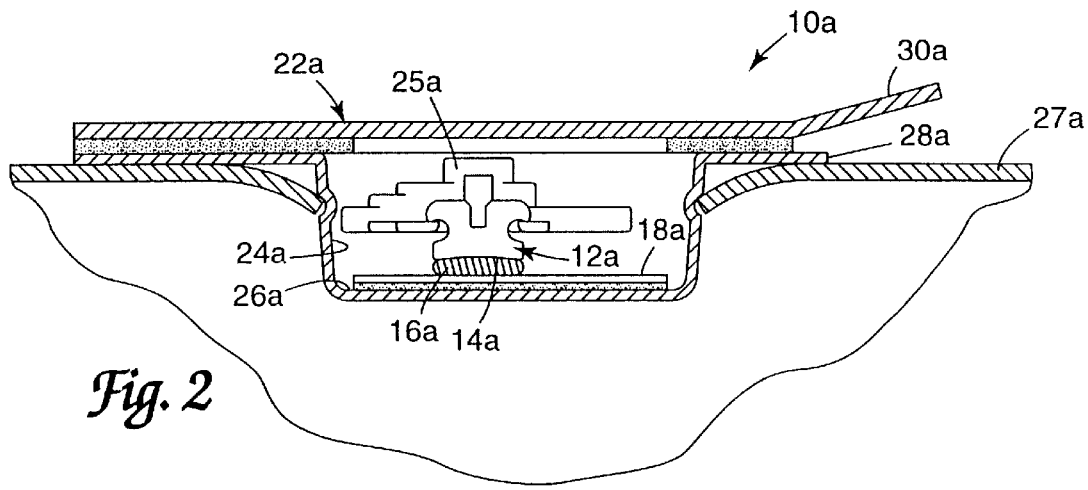
FIG. 2 is a side cross-sectional view of an orthodontic article according to another embodiment of the invention, wherein the article includes an appliance, an adhesive on the base of the appliance, a release substrate in contact with the adhesive and a container, and wherein the release substrate is fixed to the bottom of a well of a container.

In this embodiment, the bracket 12a, the adhesive 16a and the release substrate 18a are surrounded by a container 22a. The exemplary container 22a illustrated in FIG. 2 includes internal wall portions that define a well 24a with a bottom 26a. Additionally, the bracket 12a is detachably connected to a placement jig 25a to facilitate placing the bracket 12a on a tooth during bonding.

The well 24a has an oval shape in plan view. Optionally, side walls of the well 24a include horizontally extending recesses for engagement with edge structure of a carrier 27a.

Additional information regarding the carrier 27a is set out in U.S. Pat. No. 5,328,363 which is incorporated by reference herein.

The container 22a includes a flat top flange 28a, and a cover 30a is connected to the flange 28a to initially close the well 24a. Optionally, the container 22a including the well 24a, the flange 28a and the cover 30a are made of a material that provides a substantial barrier to the transmission of water vapor and oxygen. If the adhesive 16a is light-curable, it is preferable that the container 22a provides a substantial barrier to the passage of actinic radiation to the adhesive 16a when the cover 30a is closed. Optionally, the cover 30a or alternatively the well 24a transmits light in a portion of the visible spectrum so that the practitioner can visually ascertain whether or not the bracket 12a is in the well 24a.

In this embodiment, the release substrate 18a is securely fixed to the bottom 26a of the well 24a. As one example, the bottom surface of the release substrate 18a may be coated with a layer of an adhesive for securely fixing the release substrate 18a to the bottom 26a. As other examples, the release substrate 18a may be heat bonded, sonically welded and/or fused to the bottom 26a. As another alternative, the release substrate 18a may be retained in place by an interference fit that is created by cutting the release substrate 18a to a size that is slightly larger than the periphery of the well 24a adjacent the bottom 26a, and in this embodiment the elastic properties of the release substrate 18a can be employed to help retain the release substrate 18a in place.

The bracket 12a, the adhesive 16a and the release substrate 18a may be identical to the bracket 12, the adhesive 16 and the release substrate 18 as described above. When the release substrate 18a is made of a resilient, compressible material such as a polymeric foam, the release substrate 18a provides a cushion to help protect the bracket 12a during shipment and subsequent handling prior to use. Optionally, the release substrate 18a is partially compressed when the cover 30a is closed, in order to ensure that the bracket 12a does not unintentionally shift within the well 24a and unduly disturb the shape of the adhesive 16a. As another option, one or more additional sections of foam material may be added to the well 24a or to the underside of the cover 30a to provide further cushioning for the bracket 12a.

Optionally, the adhesive 16a is initially applied to the release substrate 18a instead of to the bracket 12a during manufacture of the article 10a. Furthermore, a number of "pillows" or "buttons" of the adhesive 16a could be applied to a strip or roll of material used to make the release substrate 18a, and a robotic arm is then used to place a bracket 12a on top of each adhesive button in a selected orientation and with a selected pressure. The strip or roll of material is then die-cut around each bracket 12a to fit the well 24a and each section of substrate 18a is transferred to a container 22a (which, is optionally part of a web that is later cut to provide individual, discrete containers 22a). In this option, the bracket 12a may be heated if desired to facilitate full transfer of the top layer of the adhesive button to the mesh or other retention structure (if provided) of the bracket base. As an additional option, the adhesive button may be cooled to facilitate handling as described in U.S. Pat. No. 5,552,177 which is incorporated by reference herein.

Figure 3:
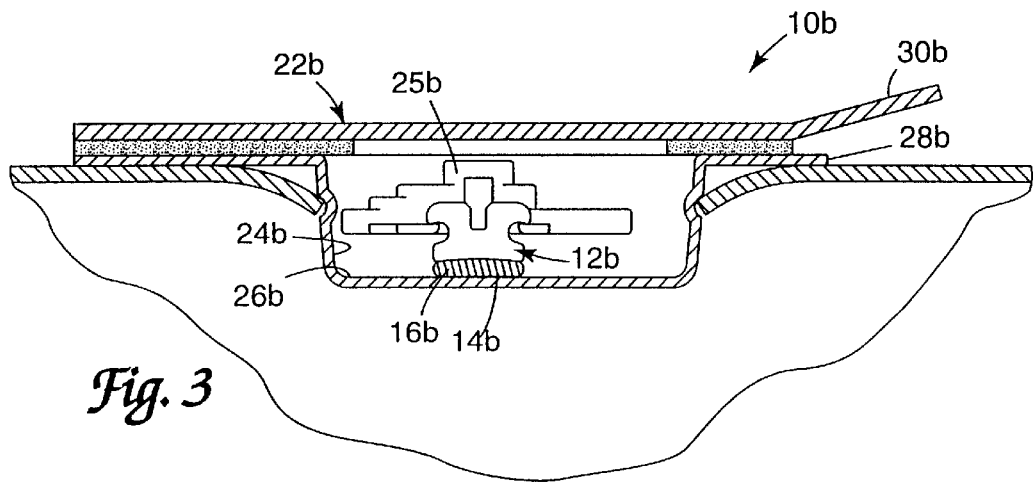
FIG. 3 is a side cross-sectional view of an orthodontic article according to another embodiment of the invention that is somewhat similar to the article in FIG. 2, except that the release substrate is an integral part of the container bottom.

An orthodontic article 10b according to yet another embodiment of the invention is illustrated in FIG. 3. The article 10b includes a bracket 12b having a base 14b, and an adhesive 16b extends across the base 14b. The bracket 12b and the adhesive 16b are identical to the bracket 12 and the adhesive 16 respectively described above.

The article 10b also includes a container 22b. The container 22b is identical to the container 22a, except that the container 22b has a bottom 26b that includes structure providing a release substrate identical to the release substrate 18 described above when certain materials are used for making the bottom 26b. For example, the bottom 26b could include a number of pores identical to the pores described above, so that a separate substrate is not needed. As an alternative, the bottom 26b, either having pores or lacking pores, could be coated with a liquid composition that is similar or identical to the liquid compositions mentioned above.

Figure 4:
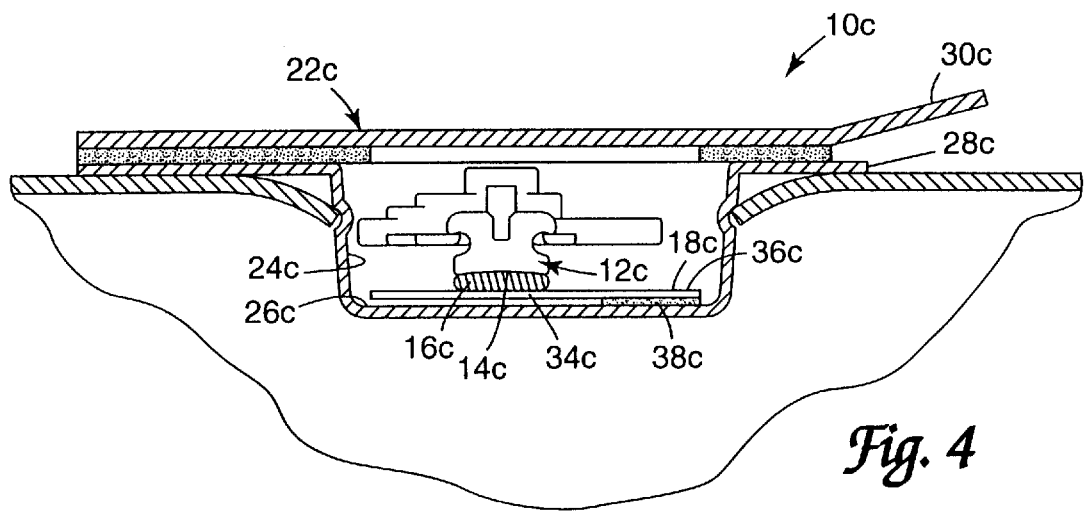
FIG. 4 is a side cross-sectional view of an orthodontic article according to another embodiment of the invention wherein the article includes an orthodontic appliance, an adhesive on the base of the appliance, a release substrate in contact with the adhesive and a container initially enclosing the appliance, the adhesive and the release substrate.
Figure 5:
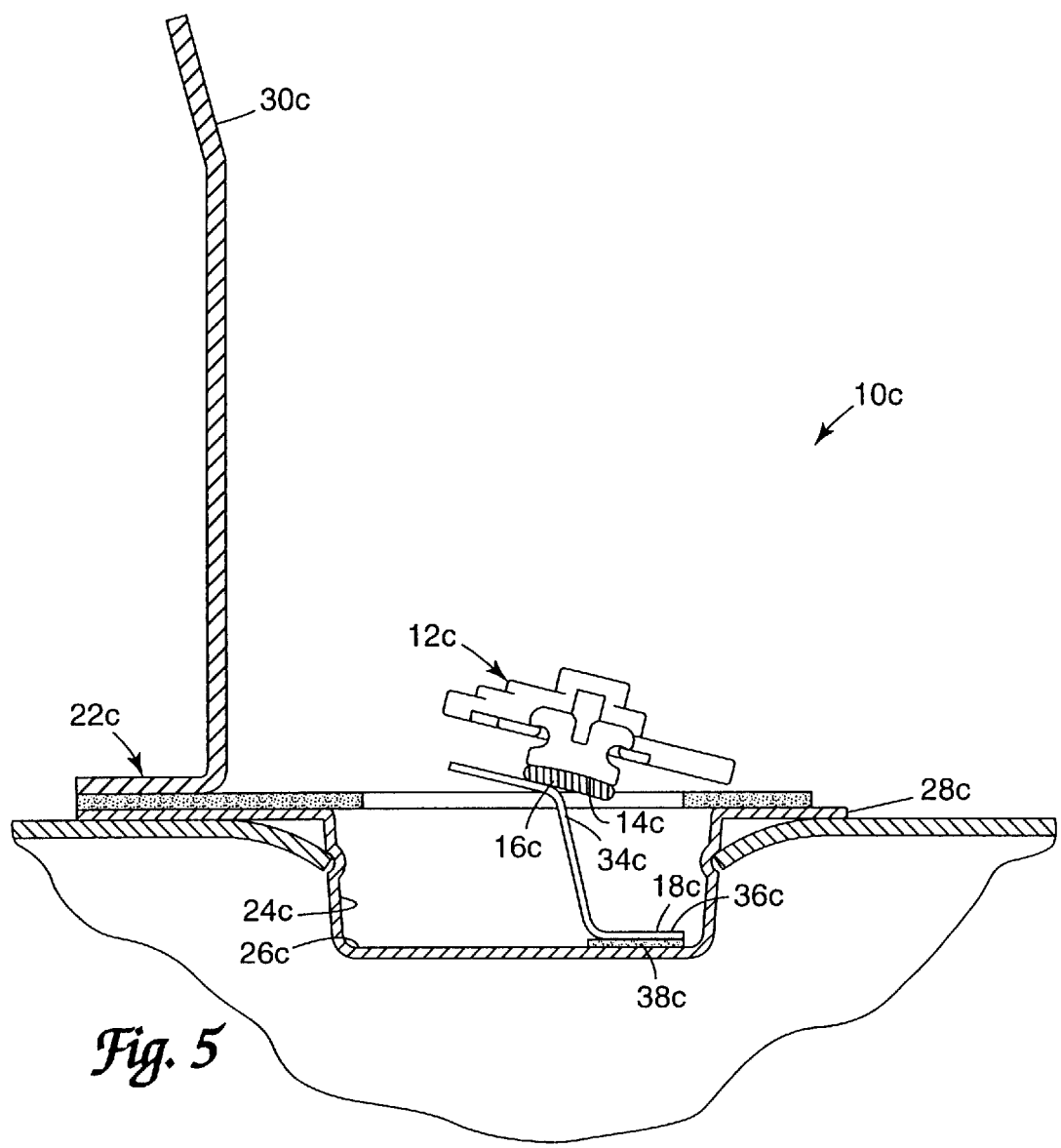
FIG. 5 is a view somewhat similar to FIG. 4 except that a cover of the container has been opened and the appliance has been lifted from a well of the container.

An article 10c according to another embodiment of the invention is illustrated in FIGS. 4 and 5. The article 10c includes a bracket 12c, an adhesive 16c on a base of the bracket 12c and a release substrate 18c in contact with the adhesive 16c.

A container 22c initially encloses the bracket 12c, the adhesive 16c and the release substrate 18c. The container 22c includes a well 24c having a bottom 26c. The container 22c also includes a top flange 28c that is connected to a cover 30c.

The bracket 12c, the adhesive 16c and the container 22c are identical to the bracket 12, the adhesive 16 and the container 22a described above. The release substrate 18c is identical to the release substrate 18a, except that the release substrate 18c is connected in a somewhat different fashion to the bottom 22c. In all other aspects, the release substrate 18c is identical to the release substrate 18 described above.

The adhesive 16c is located on a first section 34c of the release substrate 18c. A second section 36c of the release substrate 18c is spaced from the first section 34c and is connected by an adhesive 38c directly to a portion of the well bottom 26c. A suitable adhesive for fixing the second section 36c to the well bottom 26c is a pressure sensitive adhesive, although other adhesives or joining techniques could be used as well.

As the bracket 12c is lifted from the well 24c, the release substrate 18c moves away from the well bottom 26c in the manner shown in FIG. 5 to assume a somewhat reversed "S"-shaped configuration. Continued movement of the bracket 12c away from the bottom 26c peels the first section 34c away from the adhesive 16c such that separation between the adhesive 16c and the first section 34c substantially occurs along a line or narrow band that advances toward the left-hand side of FIG. 5. In this manner, only a relatively small area of adhesive 16c is directly adjacent the separating surfaces at any one time. The peeling effect facilitates separation of the adhesive 16c from the release substrate 18c while leaving the adhesive 16c substantially undisturbed and in contact with the base of the bracket 12c.

In other respects, the container 22c (as well as the containers 22a, 22b) is similar or identical to the structure described in the aforementioned U.S. Pat. No. 5,328,363, which is incorporated by reference herein. The reader is referred to that patent for additional information if desired.

In all of the various embodiments above, the release substrate and/or the liquid composition facilitates separation of the adhesive from the substrate in a manner far superior to previously known techniques. As such, the invention is especially suitable for use with adhesives that have a relatively low viscosity, with adhesives that are more tacky and/or with adhesives that have less cohesive strength than adhesives currently known or used with adhesive precoated brackets. As such, the invention enables the use of adhesives having a wider variety of characteristics than previously possible.

Those skilled in the art may recognize that a number of modifications and additions may be employed in connection with the specific, presently preferred, embodiments described above and illustrated in the accompanying drawings. As such, the invention should not be deemed limited to the particular embodiments set out in detail, but instead only by a fair scope of the claims that follow along with their equivalents.

What is claimed is:

1. An article comprising:
   an orthodontic appliance having a base for bonding the appliance to a tooth;
   an adhesive on the base of the appliance; and
   a release substrate having an exterior surface in contact with the adhesive, the exterior surface having a number of pores, wherein less than about 50% of the adhesive by weight is within the pores.

2. An article according to claim 1 wherein the pores have openings generally ranging in area from about 0.00005 inch to about 0.03 inch.

3. An article according to claim 1 wherein the release substrate is a foam.

4. An article according to claim 3 wherein the foam is a polymeric foam.

5. An article according to claim 4 wherein the polymeric foam comprises polyolefin.

6. An article according to claim 3 wherein the foam is coated with a barrier material.

7. An article according to claim 6 wherein the barrier material is a curable composition.

8. An article according to claim 3 wherein the foam is fused to provide a barrier surface.

9. An article according to claim 3 wherein the release substrate includes a liquid composition on the foam and in contact with the adhesive to facilitate release of adhesive from the foam.

10. An article according to claim 1 wherein the substrate is compressible.

11. An article according to claim 10 wherein the substrate comprises polymeric foam.

12. An article according to claim 1 wherein the article includes a container surrounding the appliance, and wherein the release substrate is fixed to the container.

13. An article according to claim 12 wherein the container has a well with a bottom, and wherein the release substrate is secured to the bottom.

14. An article according to claim 13 wherein the release substrate extends across the bottom and remains extending across the bottom as the appliance is lifted from the well.

15. An article according to claim 13 wherein the release substrate has a first section in contact with the adhesive and a second section spaced from the first section, wherein the second section is connected to the bottom and wherein the first section is movable away from the bottom when the appliance is lifted from the well.

16. An article according to claim 12 wherein the container has a well with a bottom, and wherein the release substrate is integral with the bottom.

17. An article according to claim 12 wherein the article includes projecting or released structure at least partially surrounding the base of the appliance for hindering lateral movement of the adhesive.

18. An article according to claim 17 wherein the release substrate includes the projecting or recessed structure.

19. An article according to claim 1 wherein the exterior surface of the release substrate is a microreplicated surface.

20. An article according to claim 1 wherein the exterior surface of the release substrate has spaced apart particles providing a number of pores.

21. An article according to claim 20 wherein the particles have a generally spherical configuration.

22. An article according to claim 20 wherein the particles have an irregular shape.

23. An article according to claim 1 wherein at least 50% of the volume of the pores is free of adhesive.

24. An article according to claim 1 wherein at least 75% of the volume of the pores is free of adhesive.

25. An article according to claim 1 wherein less than about 75% of the weight of the adhesive is within the pores.

26. An article according to claim 1 wherein less than about 90% of the weight of the adhesive is within the pores.

27. An article comprising:
   an orthodontic appliance having a base for bonding the appliance to a tooth;
   an adhesive on the base of the appliance; and
   a release substrate having an exterior surface in contact with the adhesive, the exterior surface including a liquid composition, and wherein at least a portion of the liquid composition remains in contact with the adhesive when the appliance and the adhesive are released from the substrate.

28. An article according to claim 27 wherein the liquid composition polymerizes with the adhesive as the adhesive hardens.

29. An article according to claim 28 wherein the liquid composition is at least partially crosslinked into the adhesive as the adhesive hardens.

30. An article according to claim 27 wherein the liquid composition has a molecular weight that is less than the molecular weight of the adhesive.

31. An article according to claim 27 wherein the liquid composition comprises one or more monomers, oligomers, polymers, copolymers or blends thereof.

32. An article according to claim 27 wherein the liquid composition includes additives selected from a group consisting of pigments, antioxidants and curatives.

33. An article according to claim 27 wherein the liquid composition includes solid filler particles.

34. An article according to claim 27 wherein the liquid composition includes fluoride releasing materials.

35. An article according to claim 27 wherein the liquid material includes a material that etches tooth enamel.

36. An article according to claim 27 wherein the liquid composition comprises one or more hydrophilic monomers, one or more hydrophilic oligomers, one or more hydrophilic polymers or blends thereof.

37. An article according to claim 27 wherein the liquid composition extends across substantially all of the adhesive in areas where the adhesive contacts the release substrate.

38. An article according to claim 27 wherein the liquid extends across only a portion of the adhesive in areas where the adhesive contacts the release substrate.

39. An article according to claim 27 and including a container surrounding the article, wherein the release substrate is fixed to the container.

40. An article according to claim 39 wherein the container includes a well with a bottom, and wherein the release substrate is secured to the bottom.

41. An article according to claim 39 wherein the release substrate is integral with the bottom.

42. An article according to claim 27 wherein the exterior surface of the release substrate is a microreplicated surface.

43. An article according to claim 27 wherein the exterior surface has a number of pores.

44. An article according to claim 43 wherein less than about 50% of the adhesive by weight is within the pores.

45. An article according to claim 43 wherein less than about 75% of the adhesive by weight is within the pores.

46. An article according to claim 27 wherein the exterior surface of the release substrate has spaced apart particles providing a number of pores.

47. An article according to claim 27 wherein the liquid composition is substantially immiscible with the adhesive.

48. An article according to claim 27 wherein the article includes projecting or released structure at least partially surrounding the base of the appliance for hindering lateral movement of the adhesive.

49. An article according to claim 48 wherein the release substrate includes the projecting or recessed structure.

50. An article comprising:
an orthodontic adhesive having a base for bonding the appliance to a tooth;
an adhesive on the base of the appliance; and
a release substrate having an exterior surface in contact with the adhesive, the release substrate comprising a foam.

51. An article according to claim 50 wherein the foam is a polymeric foam.

52. An article according to claim 51 wherein the polymeric foam comprises polyolefin.

53. An article according to claim 50 wherein the release substrate includes a liquid composition on the foam and in contact with the adhesive to facilitate release of adhesive from the foam.

54. An article according to claim 53 wherein the liquid composition polymerizes with the adhesive as the adhesive hardens.

55. An article according to claim 54 wherein the liquid composition is at least partially crosslinked into the adhesive as the adhesive hardens.

56. An article according to claim 53 wherein the liquid composition has a molecular weight that is less than the molecular weight of the adhesive.

57. An article according to claim 53 wherein the liquid composition comprises one or more hydrophilic monomers, one or more hydrophilic oligomers, one or more hydrophilic polymers or blends thereof.

58. An article according to claim 53 wherein the liquid material includes a material that etches tooth enamel.

59. An article according to claim 53 wherein the liquid composition is substantially immiscible with the adhesive.

60. An article according to claim 50 wherein the article includes projecting or released structure at least partially surrounding the base of the appliance for hindering lateral movement of the adhesive.

61. An article according to claim 50 wherein the substrate is compressible.

62. An article according to claim 50 wherein the foam includes pores having openings generally ranging in area from about 0.00005 inch to about 0.03 inch.

63. An article according to claim 50 wherein the article includes a container surrounding the appliance, wherein the container has a well with a bottom and wherein the release substrate is secured to the bottom.

64. An article according to claim 50 wherein less than about 75% of the weight of the adhesive is within the pores.

65. An article according to claim 50 wherein less than about 90% of the weight of the adhesive is within the pores.

* * * * *